US008852115B2

(12) United States Patent
Muir

(10) Patent No.: US 8,852,115 B2
(45) Date of Patent: Oct. 7, 2014

(54) PATIENT MONITORING SYSTEMS WITH GOAL INDICATORS

(75) Inventor: Randall Muir, Golden, CO (US)

(73) Assignee: Covidien LP, Mansfield, MA (US)

( * ) Notice: Subject to any disclaimer, the term of this patent is extended or adjusted under 35 U.S.C. 154(b) by 408 days.

(21) Appl. No.: 13/174,446

(22) Filed: Jun. 30, 2011

(65) Prior Publication Data

US 2013/0006129 A1 Jan. 3, 2013

(51) Int. Cl.

| | |
|---|---|
| ***A61B 5/02*** | (2006.01) |
| ***A61B 5/00*** | (2006.01) |
| ***A61B 5/0245*** | (2006.01) |
| ***A61B 5/1455*** | (2006.01) |

(52) U.S. Cl.

CPC ........... *A61B 5/1455* (2013.01); *A61B 5/02455* (2013.01); *A61B 5/742* (2013.01); *A61B 5/746* (2013.01)

USPC ............................ 600/500; 600/300; 600/323

(58) Field of Classification Search

USPC ................................. 600/310–344, 500–507

See application file for complete search history.

(56) References Cited

U.S. PATENT DOCUMENTS

| | | | | |
|---|---|---|---|---|
| 5,438,983 | A | 8/1995 | Falcone | |
| 5,830,135 | A | 11/1998 | Bosque et al. | |
| 5,865,736 | A * | 2/1999 | Baker et al. | 600/323 |
| 5,920,263 | A | 7/1999 | Huttenhoff et al. | |
| 6,606,511 | B1 | 8/2003 | Ali et al. | |
| 6,658,276 | B2 * | 12/2003 | Kianl et al. | 600/322 |
| 6,684,090 | B2 | 1/2004 | Ali et al. | |
| 6,754,516 | B2 | 6/2004 | Mannheimer | |
| 6,822,564 | B2 | 11/2004 | Al-Ali | |
| 6,996,427 | B2 | 2/2006 | Ali et al. | |
| 7,030,749 | B2 | 4/2006 | Al-Ali | |
| 7,123,950 | B2 | 10/2006 | Mannheimer | |
| 7,375,347 | B2 | 5/2008 | Colvin et al. | |
| 7,378,954 | B2 | 5/2008 | Wendt | |
| 7,398,115 | B2 | 7/2008 | Lynn | |
| 7,415,297 | B2 | 8/2008 | Al-Ali et al. | |
| 7,460,899 | B2 | 12/2008 | Almen | |
| 2003/0018241 | A1 * | 1/2003 | Mannheimer | 600/300 |

(Continued)

FOREIGN PATENT DOCUMENTS

| | | | | |
|---|---|---|---|---|
| GB | 2368124 | * 4/2002 | | A61B 5/024 |
| JP | 2006061566 | A2 | 3/2006 | |

OTHER PUBLICATIONS

Lutter, Norbert O., et al.; "False Alarm Rates of Three Third-Generation Pulse Oximeters in PACU, ICU and IABP Patients," Anesth Analg, vol. 94, pp. S69-S75 (2002).

(Continued)

*Primary Examiner* — Patricia Mallari
*Assistant Examiner* — Tiffany Weston
(74) *Attorney, Agent, or Firm* — Fletcher Yoder, P.C.

(57) ABSTRACT

Embodiments of the present disclosure relate to patient monitors designed to display goal indicators showing progress toward achieving patient monitoring goals. The goal indicators may be displayed on a main monitoring screen of the patient monitors, allowing caretakers to easily evaluate how effective they have been in managing the patient's condition. According to certain embodiments, the goal indicators may display a numerical value indicating the percentage of time that a physiological parameter, such as $SpO_2$ or pulse rate, was within predetermined goal limits. The patient monitors further may include user interfaces that enable a clinician to adjust parameters of the goal indicators, such as the goal limits and/or the goal time frame.

20 Claims, 7 Drawing Sheets

138
140 DETERMINE GOAL LIMITS
142 DETERMINE GOAL TIME FRAME
144 IDENTIFY EXCURSION EVENTS
146 CALCULATE TIME IN GOAL
148 DISPLAY/UPDATE GOAL INDICATOR
150 DETERMINE ALARMS

(56) References Cited

U.S. PATENT DOCUMENTS

2003/0078480 A1* 4/2003 Claure et al. .................. 600/323
2003/0100040 A1 5/2003 Bonnecaze et al.
2004/0133087 A1 7/2004 Ali et al.
2004/0138540 A1 7/2004 Baker et al.
2004/0215069 A1 10/2004 Mannheimer
2007/0032714 A1 2/2007 Mannheimer
2007/0109115 A1 5/2007 Kiani et al.
2007/0142716 A1 6/2007 Biondi
2007/0282181 A1 12/2007 Findlay et al.
2008/0091092 A1 4/2008 Al-Ali
2008/0183057 A1 7/2008 Taube
2008/0183058 A1 7/2008 Mannheimer
2008/0188733 A1 8/2008 Al-Ali et al.
2008/0221418 A1 9/2008 Al-Ali et al.
2008/0221464 A1 9/2008 Al-Ali
2008/0228052 A1* 9/2008 Al-Ali ........................... 600/323
2008/0300471 A1 12/2008 Al-Ali et al.
2008/0300474 A1 12/2008 Benni et al.
2009/0005703 A1* 1/2009 Fasciano ....................... 600/561
2009/0221890 A1* 9/2009 Saffer et al. ................... 600/347

OTHER PUBLICATIONS

Barnum, P.T., et al.; "Novel Pulse Oximetry Technology Capable of Reliable Bradycardia Monitoring in the Neonate," Respiratory Care, vol. 42, No. 1, p. 1072 (Nov. 1997).

International Search Report & Written Opinion for PCT No. PCT/US2012/044862 dated Oct. 17, 2012; 10 pages.

* cited by examiner

PATIENT MONITORING SYSTEMS WITH GOAL INDICATORS

BACKGROUND

The present disclosure relates generally to patient monitoring systems and, more particularly, to patient monitoring systems designed to display goal indicators depicting progress toward achieving patient monitoring goals.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

In the field of medicine, doctors often desire to monitor certain physiological characteristics of their patients. Accordingly, a wide variety of devices have been developed for monitoring many such characteristics of a patient. Such devices provide doctors and other healthcare personnel with the information they need to provide the best possible healthcare for their patients. As a result, such monitoring devices have become an indispensable part of modern medicine.

Patient monitors include medical devices that facilitate measurement and observation of patient physiological data. For example, pulse oximeters are a type of patient monitor. A typical patient monitor cooperates with a sensor to detect and display a patient's vital signs (e.g., temperature, pulse rate, respiratory rate) and/or other physiological measurements (e.g., water content of tissue, blood oxygen level) for observation by a user (e.g., clinician). For example, pulse oximeters are generally utilized with related sensors to detect and monitor a patient's functional oxygen saturation of arterial hemoglobin (i.e., $SpO_2$) and pulse rate. Other types of patient monitors, such as blood pressure monitors, may be utilized to detect and monitor other physiological parameters. Further, the patient monitors may be incorporated into other types of medical devices, such as mechanical ventilators and anesthesia machines, among others.

A patient monitor may be designed to alert a caregiver when certain physiological conditions are recognized. For example, a pulse oximeter may produce a visual and/or audible alarm when a patient's oxygen saturation falls below a predetermined threshold. The predetermined alarm thresholds may be set by the patient monitor, and, in certain circumstances, may be customizable by a user. Further, in addition to alarm thresholds, a patient monitor may be designed to provide more complex alarm features. For example, a patient monitor may be designed to display trends showing historical alarm data. The trends may be designed to display predetermined ranges of data and may be accessed by navigating through menus and/or screens of the patient monitor, which may complicate access to the historical data.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

Figure 1:
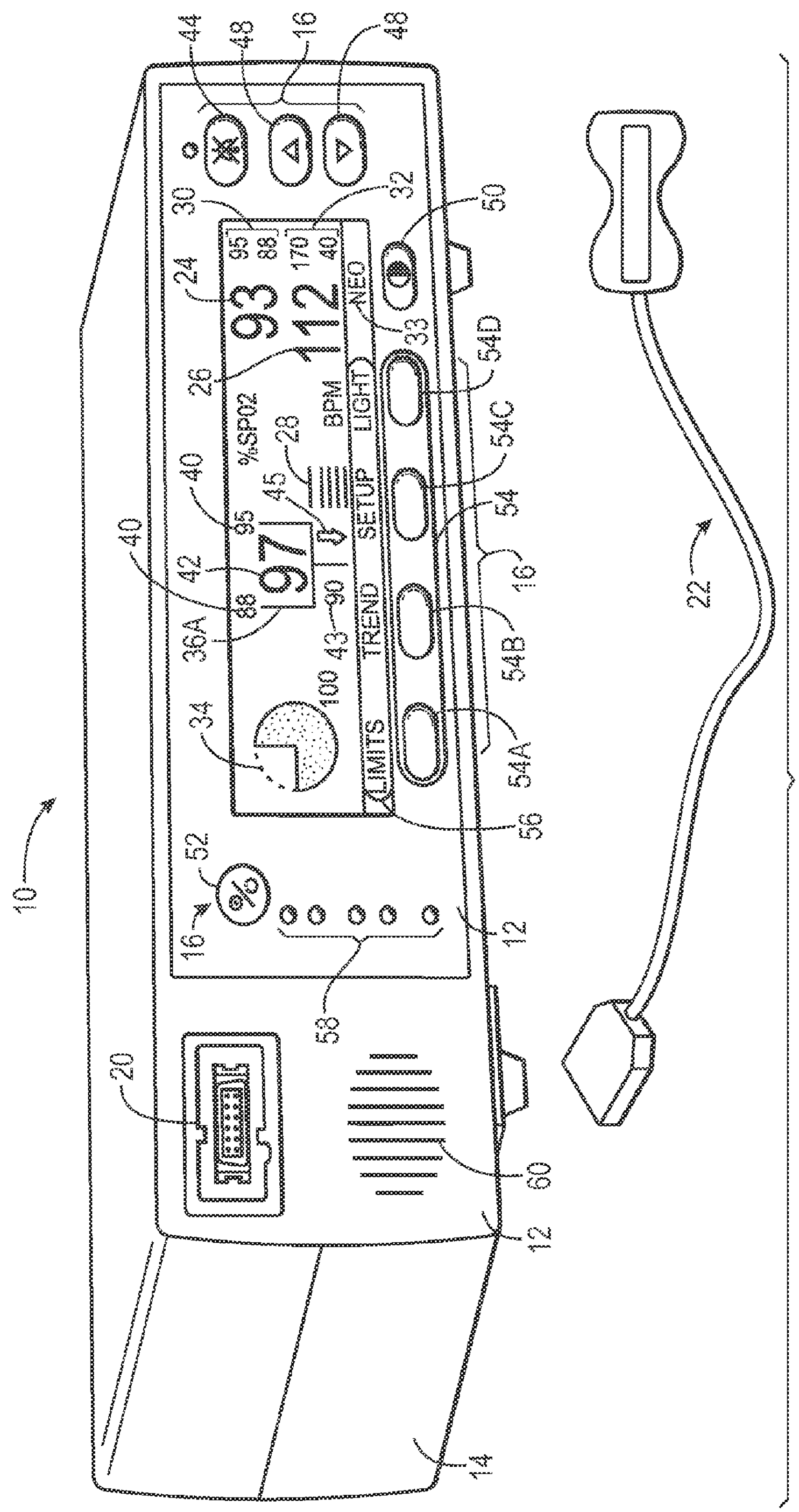
FIG. 1 is a perspective view of an embodiment of a patient monitor that may employ goal indicators that show progress toward achieving patient monitoring goals.

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to patient monitors designed to display goal indicators showing progress toward achieving patient monitoring goals. The goal indicators may be displayed on a main monitoring screen of the patient monitors, allowing caretakers to easily evaluate how effective they have been in managing the patient's condition. According to certain embodiments, the goal indicators may display a numerical value indicating the percentage of time that a physiological parameter, such as $SpO_2$ or pulse rate, was within predetermined goal limits. For example, the patient monitors may calculate the percentage of time that the physiological parameter was within the goal limits over a time frame, such as a rolling 24-hour or 12-hour period, among others. The patient monitors further may include user interfaces that enable a clinician to adjust parameters of the goal indicators, such as the goal limits and/or the goal time frame. For example, in certain embodiments, the goal limits may be set to correspond to existing alarm limits or may be set tighter or looser than certain alarm limits.

The goal indicators may be designed to provide immediate feedback to caretakers indicating how well a patient's physiological parameters have been maintained within a certain range, which may result in tighter control of patient physiological parameters, and therefore, improved patient outcomes. For example, the goal indicators may be employed to maintain a patient's $SpO_2$ above a lower limit designed to avoid or to minimize insufficient oxygenation of the arterial blood, often referred to as hypoxemia, and/or below an upper limit designed to avoid or to minimize excessive oxygenation of the blood, often referred to as hyperoxemia. It may be particularly desirable to monitor for hyperoxemia, in addition to hypoxemia, in neonatal intensive care units (NICU) to prevent outcomes that are common in premature infants, such as retinopathy of prematurity (ROP) and bronchopulmonary dysplasia (BPD). It also may be beneficial to monitor for hyperoxemia, in addition to hypoxemia, in adult patients to inhibit the suppression of respiratory drive that can be caused by hyperoxemia. However, in other embodiments, the goal indicators may be employed to promote control of a physiological parameter above a lower limit or below an upper limit. For example, the goal indicators may be employed to maintain a patient's SpO2 above a lower limit to avoid or to minimize hypoxemia. Further, in yet other embodiments, the goal indicators may be employed to maintain other physiological parameters, such as pulse rate, within a certain range.

FIG. 1 is a perspective view of an embodiment of a patient monitor 10 that may display goal indicators showing a percentage of time that a physiological parameter was maintained within predetermined goal limits. For example, the patient monitor 10 may be a pulse oximeter, such as those available from Nellcor Puritan Bennett LLC of Boulder, Colo. As shown, the patient monitor 10 is a pulse oximeter designed to detect and monitor blood oxygen saturation levels, pulse rate, and so forth. However, in other embodiments, the goal indicators may be employed in other types of patient monitors, such as vital signs monitors, critical care monitors, obstetrical care monitors, or blood pressure monitors, among others. Further, the patient monitor 10 may be part of a therapeutic medical device, such as a mechanical ventilator or anesthesia machine, among others.

The patient monitor 10 includes a front panel 12 coupled to a body 14 of the patient monitor 10. The front panel 12 may include several selectable inputs 16 that may be actuated by a caretaker to operate the patient monitor 10. For example, the selectable inputs 16 may include buttons that may be pressed to change information shown on a display 18. In other embodiments, the size, shape, locations, and/or labels for the selectable inputs 16 may vary. For example, the selectable inputs 16 may be arranged on different parts of the patient monitor 10 and/or located on an external device. In another example, some or all of the selectable inputs 16 may be graphical elements selected through a touch screen of the patient monitor 10 or through a touch screen of an external device. Further, some or all of the selectable inputs 16 may include different types of inputs, such as knobs, buttons, slide bars, joysticks, and/or wheels, among others.

In certain embodiments, the display 18 may include a cathode ray tube or liquid crystal display. Moreover, the display 18 may include an optional touch screen. In general, the display 18 may show processed physiological data and/or other data received through a medical device interface 20, such as a cable connection port, from a patient sensor 22, or other suitable medical device, such as a therapy device. As shown, the medical device interface 20 includes a cable connection port. However, in other embodiments, the medical device interface 20 may any suitable type of interface for connecting to a medical device. For example, in certain embodiments, the medical device interface 20 may include a wireless interface.

According to certain embodiments, the display 18 may be used to display an oxygen saturation 24 and/or a pulse rate 26. The oxygen saturation 24 may be a functional arterial hemoglobin oxygen saturation measurement displayed as units of percentage $SpO_2$. The pulse rate 26 may indicate a patient's pulse rate in beats per minute. The display 18 also may be used to display a blip bar 28 that displays the relative pulse amplitude. Although the display 18 is currently shown displaying a monitoring mode, which provides a monitoring overview that is easy to read from a distance, the display 18 also may be used to show topic-specific screens related to the physiological data. For example, the display 18 may be used to show a plethysmographic ("pleth") waveform display that allows visual monitoring of the pleth waveform. Moreover, the display 18 may be used to display user interface options, such as a setup and/or configuration screen for adjusting parameters such as alarm volume, display scales, alarm limits, and goal limits employed by the goal indicators, among others.

In addition to displaying physiological information, the patient monitor 10 also may display information related to alarms and monitor settings on the display 18. For example, the display 18 may display alarm limits 30 and 32 for the oxygen saturation 24 and the pulse rate 26, respectively. If an alarm limit 30 or 32 is exceeded, the patient monitor 10 may produce a visible and/or audible alarm. The display 18 also may show an indicator 33 that describes the specific mode to which the alarm limits are set. For example, the indicator 33 is currently showing "NEO" to inform a caretaker that neonatal alarm limits are currently applied, rather than adult alarm limits. The display 18 also may display indicators 34 and 36 that facilitate management of alarms and/or patient physiological parameters. For example, in some embodiments, the patient monitor 10 may employ SatSeconds™ by Nellcor™ to detect alarms and manage nuisance alarms. SatSeconds™ may include activation of an alarm based on limits that may include the integral of time and depth of a desaturation event and may include an indicator 34 that may serve to inform the caregiver that an $SpO_2$ reading has been detected outside of the limit settings.

According to certain embodiments, the SatSeconds™ alarm management feature may analyze $SpO_2$ excursions outside of the alarm limits 30 to differentiate between clinically significant desaturations and minor transient events. For example, SatSeconds™ may enable oxygen saturation alarms only when a SatSeconds™ value, represented by a combination of the magnitude and time of the oxygen saturation excursion, exceeds a certain threshold. In general, the SatSeconds™ value may be the product of the magnitude and duration of an oxygen desaturation event. Accordingly, shallow and/or short desaturation readings that may be measurement noise (e.g., that otherwise may trigger nuisance alarms) may not produce an alarm, allowing caregivers to put brief desaturation events into context with their depth and to put shallow desaturations into context with their duration. In summary, the SatSeconds™ alarm management feature may filter out nuisance alarms to produce a higher ratio of alarms when a clinically significant excursion occurs, as determined by the SatSeconds™ setting. Further, in certain embodiments, other types of alarm management features may be employed instead of, or in addition to, the SatSeconds™ alarm management feature. For example, as discussed further below with respect to FIG. 6, when the monitor 10 is operating in an adult monitoring mode, a Saturation Pattern Detection ("SPD") alarm management feature may be employed to provide information related to the occurrence, frequency, and/or magnitude of patterns indicative of repetitive reductions in airflow.

The display 18 also may display a goal indicator 36A, which indicates how well a patient's physiological parameters have been maintained within a certain goal range over a certain time frame. In particular, the goal indicator 36A may include a value 42 that represents the percentage of time that the oxygen saturation, as represented by $SpO_2$ values, has been maintained within goal limits 40. For example, as shown in FIG. 1, the value 42 indicates that the arterial oxygen saturation has been maintained between 88 and 95% $SpO_2$ for 97% of the time. As shown, the goal limits 40 include both an upper limit designed to abate hyperoxemia and a lower limit designed to abate hypoxemia. However, in other embodiments, the goal limits 40 may include only an upper limit or a lower limit. For example, as discussed further below with respect to FIG. 7, a lower limit 40 may be employed to ensure that a patient's oxygen saturation stays above a certain value to inhibit hypoxemia. The value 42 may be displayed within a graphic, such as the "goal posts" shown in FIG. 1, that allows a caretaker to easily distinguish the value 42, which is shown as a percentage, from the oxygen saturation 24, which also is shown as a percentage. Further, in other embodiments, the value 42 may be shown in a different color or font, and/or may be shown in a different location of the display 18, instead of, or in addition to being shown within a graphic.

As shown in FIG. 1, the goal limits 40 correspond to the $SpO_2$ alarm limits 30. Accordingly, in this embodiment, the goal indicator 36A also represents the percentage of time that the oxygen saturation has been maintained within the alarm limits 30. However, in other embodiments, the goal limits 40 may not correspond to the alarm limits 30. For example, in certain embodiments, the goal limits 40 may be set tighter than the alarm limits 30 to maintain the oxygen saturation within a tighter range than the alarm limits, which in turn, may reduce the number of alarms. Moreover, as discussed further below with respect to FIG. 10, the patient monitor 10 may include a user interface that allows a user to adjust the goal limits 40.

The goal indicator 36A also may include a goal threshold 43 that indicates the minimum percentage of time that the physiological parameter should be maintained within the goal limits 40. According to certain embodiments, the goal threshold 43 may be adjustable by a user through a user interface of the patient monitor 10. As shown in FIG. 1, the goal threshold 43 is displayed as part of the goal indicator 36A. However, in other embodiments, the goal threshold 43 may not be shown on the display 18, although the goal threshold 43 may be stored within the patient monitor 10. The patient monitor 10 may be designed to produce visible and/or audible alarms based on the goal threshold 43. For example, when the value 42 is below the goal threshold 43, a visual indicator may be provided, e.g., the goal indicator 36A may flash or change color. In another example, the patient monitor 10 may emit an audible alarm when the value 42 is below the goal threshold 43. The goal based alarm conditions may be separate from and independent of the alarm conditions associated with the alarm limits 30. For example, one sound may be emitted when an alarm is triggered based on the alarm limits 30 and another sound may be emitted when an alarm is triggered based on the goal threshold 43.

The goal indicator 36A also may include an excursion indicator 45 that indicates whether the majority of out of goal conditions have been above or below the goal limits 40. For example, as shown in FIG. 1, the excursion indicator 45 includes a down arrow, which indicates that most of the excursions have been below the lower goal limit 40. In another example, an up arrow may be displayed if most of the excursions have been above the upper goal limit 40. According to certain embodiments, a caretaker may employ the excursion indicator 45 in determining how to modify the patient's care to maintain the physiological parameter within the goal limits. For example, a caretaker may take one corrective action when the excursion indicator 45 shows that the excursions have been above the upper goal limit and may take another corrective action when the excursion indicator shows that the excursions have been below the lower goal limit. Further, in other embodiments, other types of graphics, symbols, and/or alarms may be employed to indicate the type of excursions. For example, the value 42 may be shown in a different color or a different alarm may sound depending on whether most of the excursions have been above or below the goal limits 40.

In general, the selectable inputs 16 may be used to control operating functions of the patient monitor 10. For example, when an alarm is triggered, one of the selectable inputs 16, such as an alarm silence button 44, may be actuated to silence the alarm and display an alarm silence indicator (not shown), such as a slash and a timer, on the display 18. The selectable inputs 16 also may include other fixed function keys, such as arrow keys 48, a contrast selection key 50, and a power key 52. For example, the arrow keys 48 may be actuated to adjust alarm limits, to adjust goal limits, to set the goal threshold, and/or to vary the physiological information shown on the display 18. In another example, the contrast selection key 50 may be actuated to adjust the contrast of the display 18. Further, the fixed function keys may be programmed to control multiple functions or to operate in different manners based upon various factors, such as the duration the key is pressed, the simultaneous activation of other keys, and so forth. For example, an arrow key 48 may be configured to scroll upwards or downwards more rapidly based upon how long the respective key is held down.

The monitor 10 also may include programmable function keys ("soft keys") 54, and associated soft key icons in the soft key menu 56. Each of the four soft keys 54A, 54B, 54C, and 54D may be pressed to select a corresponding function indicated by the respective soft key icon. For example, the soft key 54A may be pressed to display "LIMITS" information, while the soft key 54B may be pressed to display "TREND" information. In certain embodiments, the soft keys 54 may be programmed to display operating information such as alarm limits, historic trends, setup menus, and alarm volume settings, among others. Moreover, a caregiver may actuate the soft keys 54 to display various operating menus, and then may use the arrow keys 48 to adjust operating parameters. Further, in certain embodiments, a caregiver may navigate through the user interface of the patient monitor 10 using the soft keys 54 and the fixed function keys (e.g., 44 and 48) to adjust alarm limit settings. For example, a caretaker may select the soft key 54A to access a screen for setting goal limits and the goal threshold, as described below with respect to FIG. 10.

In addition to the selectable inputs 16, the front panel 12 may include various indicators 58 (e.g., indicator lights) that facilitate operation of the monitor 10. For example, the indicators 58 may include an A/C power indicator, a low battery indicator, an alarm silence indicator, a mode indicator, and so forth. The front panel 12 also includes a speaker 60 for emitting audible indications (e.g., alarms). For example, the speaker 60 may be employed to emit alarms based on the alarm limits 30 and/or the goal threshold 43. In other embodiments, the indicators 58 and/or the speaker 60 may be located on other locations of the patient monitor 10 or on an external device.

Figure 2:
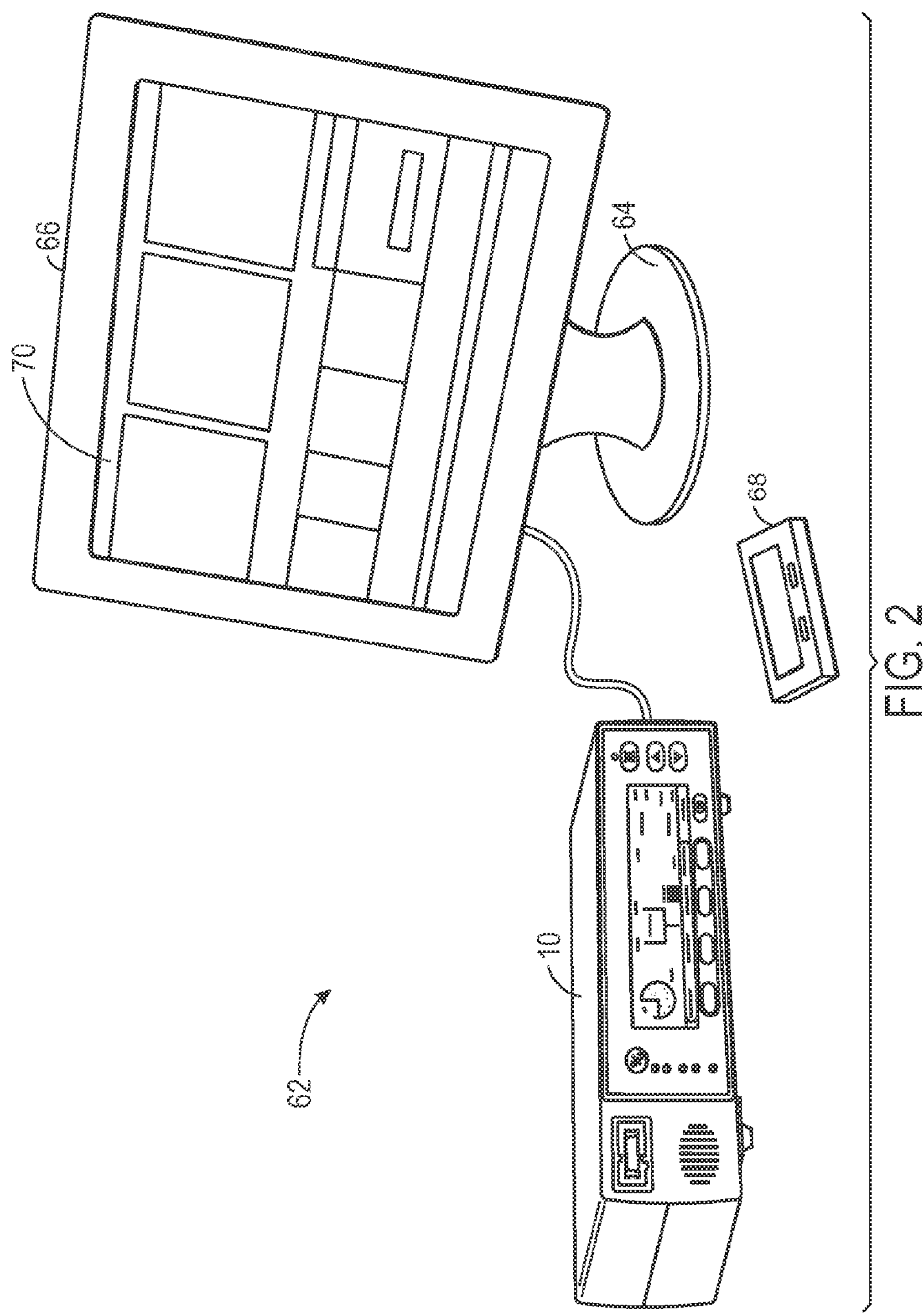
FIG. 2 is a perspective view of an embodiment of a patient monitoring system that includes the patient monitor of FIG. 1.

FIG. 2 depicts a monitoring system 62 that may employ the patient monitor 10. The monitoring system 62 includes a central station 64 that may be connected to one or more patient monitors 10 by a hardwired or wireless communication link. According to certain embodiments, the central station 64 may be a Nellcor Oxinet® III Central Station, available from Nellcor™. The central station 64 may include a display 66 that displays physiological data from the connected patient monitors 10. For example, in certain embodiments, the central station 64 may display the goal indicator 36A. The central station 64 may allow a caretaker to monitor the physiological data from several patients in a single location. Further, the central station 64 may produce corresponding alarms when a patient monitor 10 alarms. The monitoring system 62 also may include one or more pagers 68 that individual caretakers may early with them to receive alarms from the central station 64.

The central station 64 may include one or more input devices, such as a touch screen 70, that allow a user to control operations of the monitoring system 62. In other embodiments, the input devices may vary. For example, the input devices may include a keyboard, remote control, or mouse, among others. Through the input devices 70, a user may adjust alarm settings and goal settings for the connected patient monitors 10. A user also may manipulate the input devices 70 to change other setup options for the patient monitors 10 and to view information about the physiological data. For example, a user may manipulate the touch screen 70 to view trend data, alarm limits, goal limits, the goal threshold, or current settings for a patient monitor 10 that is part of the monitoring system 62.

Figure 3:
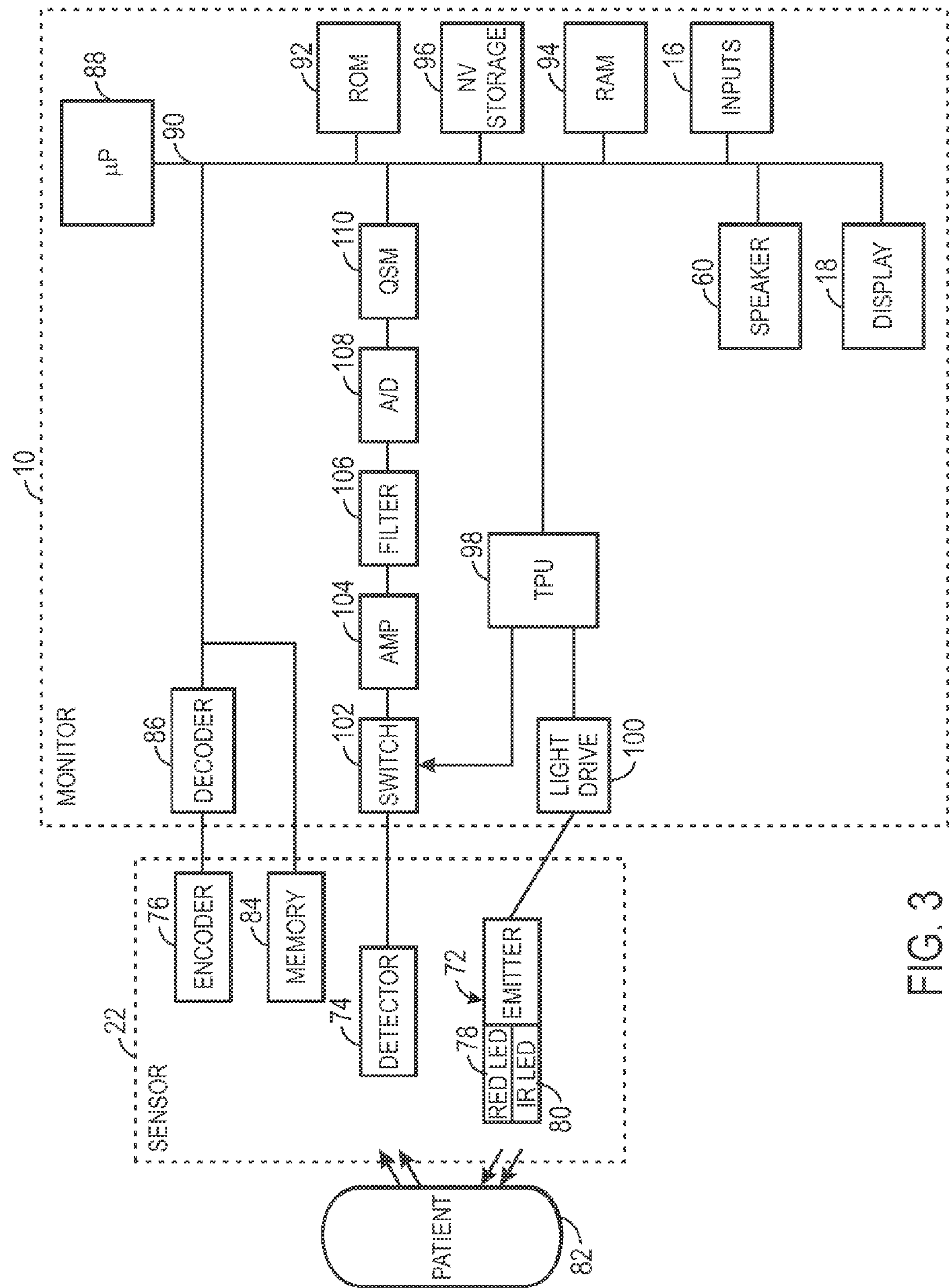
FIG. 3 is a block diagram of an embodiment of the patient monitor of FIG. 1.

Turning to FIG. 3, a simplified block diagram of a portion of the patient monitor 10 is illustrated, in accordance with certain embodiments. Specifically, certain components of the sensor 22 and the monitor 10 are illustrated in FIG. 3. The sensor 22 includes an emitter 72, a detector 74, and an encoder 76. The emitter 72 includes two light sources 78 and 80, shown here as LEDs, that are capable of emitting different wavelengths of light into the tissue of a patient 82 to measure physiological parameters of the patient 82. As shown in FIG. 3, the light source 78 represents a red LED designed to emit red light at a wavelength between about 600 nanometers (nm) and about 700 nm, and the light source 80 represents an infrared (IR) LED designed to emit IR light at a wavelength between about 800 nm and about 1000 nm. However, in other embodiments, the light sources 78 and 80 may be designed to emit light at other suitable wavelengths.

Although two light sources are shown in FIG. 3, in other embodiments, any number of one or more light sources can be included in the emitter 72. For example, in certain embodiments, the emitter 72 may include three light sources: a red light source designed to emit light red light at a wavelength between about 620 nm and about 700 nm, a far red light source designed to emit far red light at a wavelength between about 690 nm and about 770 nm, and an infrared light source designed to emit infrared light at a wavelength between about 860 nm and 940 nm. In these embodiments, different combinations of light sources may be used to measure physiological parameters depending on the current arterial oxygen saturation value. For example, when blood perfused tissue has a high arterial oxygen saturation value (e.g., greater than 84%), the $SpO_2$ value may be more accurately calculated by employing the red light source and the infrared light source. On the other hand, when blood perfused tissue has a low arterial oxygen saturation value (e.g., less than 75%), the $SpO_2$ value may be more accurately calculated by employing the far red light source and the infrared light source. When the blood perfused tissue has an intermediate arterial oxygen saturation value (e.g., between 75% and 84%), measurements may be taken using the red and infrared light sources, the near red and infrared light sources, or a combination of the red, near red, and infrared light sources (e.g., readings from the light sources may be averaged and/or weighted). In these embodiments, the light sources that are used may be selected based on a previously measured arterial oxygen saturation value.

It should be understood that, as used herein, the term "light" may refer to one or more of ultrasound, radio, microwave, millimeter wave, infrared, visible, ultraviolet, gamma ray or X-ray electromagnetic radiation, and may also include any wavelength within the radio, microwave, infrared, visible, ultraviolet, or X-ray spectra, and that any suitable wavelength of light may be appropriate for use with the present disclosure. In operation, light enters the detector 74 after passing through the tissue of the patient 82. The detector 74 may convert the light at a given intensity, which may be directly related to the absorbance and/or reflectance of light in the tissue of the patient 82, into an electrical signal. That is, when more light at a certain wavelength is absorbed or reflected, less light of that wavelength is typically received from the tissue by the detector 74. For example, the detector 74 may include one or more photodiodes, or any other element capable of converting light into either a current or voltage. After converting the received light to an electrical signal, the detector 74 may send the signal to the monitor 10, where physiological characteristics may be calculated based at least in part on the absorption of light in the tissue of the patient 82.

The sensor 12 also includes the encoder 76, which contains information about the sensor 12, such as the sensor type (e.g., whether the sensor is intended for placement on a forehead, digit, or other body part) and the wavelengths of light emitted by the light sources 78 and 80. The sensor information may allow the monitor 10 to select appropriate algorithms and/or calibration coefficients for calculating the physiological characteristics of the patient 82. According to certain embodiments, the encoder 76 may include a memory on which one or more of the following information may be stored for communication to the monitor 14: the type of the sensor 22; the wavelengths of light emitted by the light sources 78 and 80; and the proper calibration coefficients and/or algorithms to be used for calculating the physiological characteristics of the patient 82.

The sensor 12 further may include a memory 84, such as an EEPROM, flash memory, or other suitable optical, magnetic, or solid-state computer readable media, that stores data related to the goal indicator 36A. For example, the memory 84 may store data representing the goal limits 40, the goal threshold 43 and/or the duration of the goal time frame, as well as data indicating the excursions that have occurred within the time frame. According to certain embodiments, storage of goal indicator data within the sensor 22 may enable the data to be retrieved and downloaded to different monitors 10 connected to the sensor 22. For example, when the patient 82 is moved between rooms, the goal indicator data may be stored on the memory 84 and may be downloaded to the patient monitor 10 in the new room upon connection of the sensor 22 to the new patient monitor 10. As shown in FIG. 2, the memory 84 is separate from the encoder 76. However, in other embodiments, the memory 84 may be integrated with the encoder 76. Further, in yet other embodiments, the memory 84 may be omitted and the goal indicator data may not be stored on the sensor 22.

Signals from the encoder 76 can be transmitted to a detector/decoder 86 in the monitor 10 where the data and signals can be decoded. The detector/decoder 86 may decode the signals from the encoder 76 and may provide the decoded information to a processor 88. According to certain embodiments, the decoded information may represent the type of the sensor 22 and the wavelengths of light emitted by the light sources 78 and 80. The processor 88 may then use the decoded information to determine the proper method for calculating the patient's physiological characteristics. For example, the processor may use the decoded information in conjunction with algorithms or look-up tables to identify the proper calibration coefficients and/or algorithms to be used for calculating the patient's physiological characteristics.

Signals from the detector 74 also may be transmitted to the monitor 10 where the signals can be used to calculate the patient's physiological characteristics. The monitor 10 generally includes the one or more processors 88 connected to an internal bus 90. The bus 90 is also connected to the input components 16 and the display 18, as well as a read-only memory (ROM) 56, a random access memory (RAM) 58, and a nonvolatile storage 96 (such as a magnetic or solid state hard drive or memory, optical disk, or any other suitable optical, magnetic, or solid-state computer readable media) that stores longer-term data.

A time processing unit (TPU) 98 may provide timing control signals to a light drive circuitry 100, which controls when the emitter 72 is illuminated and the multiplexed timing for the light sources 78 and 80. The TPU 98 also may control the gating-in of signals from detector 74 through a switching circuit 102. These signals may be sampled at the proper time, depending upon which light source 78 or 80 is illuminated. The received signal from the detector 74 may be passed through an amplifier 104, a low pass filter 106, and an analog-to-digital converter 108 for amplifying, filtering, and digitizing the electrical signals the from the sensor 22. The digital data may then be stored in a queued serial module (QSM) 110 for later downloading to the RAM 94 as the QSM 110 fills up. In certain embodiments, there may be multiple separate parallel paths having the amplifier 104, the filter 106, and the A/D converter 108 for multiple light wavelengths or spectra received.

The processor 88 may use the digital data, as well as other signals from the detector 74 to calculate and/or determine physiological characteristics, such as oxygen saturation, pulse rate, and total hemoglobin, among others. For example, the processor 88 may use various encoded instructions, algorithms, and/or lookup tables that may be stored in the ROM 92, as well as in the nonvolatile storage 96, to calculate the physiological characteristics based at least in part upon the signals that correspond to the light received by the detector 74. According to certain embodiments, code encoding executable algorithms may be stored in the ROM 92 or the nonvolatile storage 96 and accessed and operated according to processor instructions. The calculated physiological characteristic may then be displayed on the display 18 for a caregiver to monitor or review. The processor 88 also may access and execute coded instructions for determining the goal value 42 and for displaying the goal indicator 36A. According to certain embodiments, one or more algorithms and/or lookup tables may be stored in the ROM 92 or the nonvolatile storage 96 and employed by the processor 88 to calculate the goal value 42 and to determine whether alarm conditions related to the goal value 42 have occurred.

Figure 4:
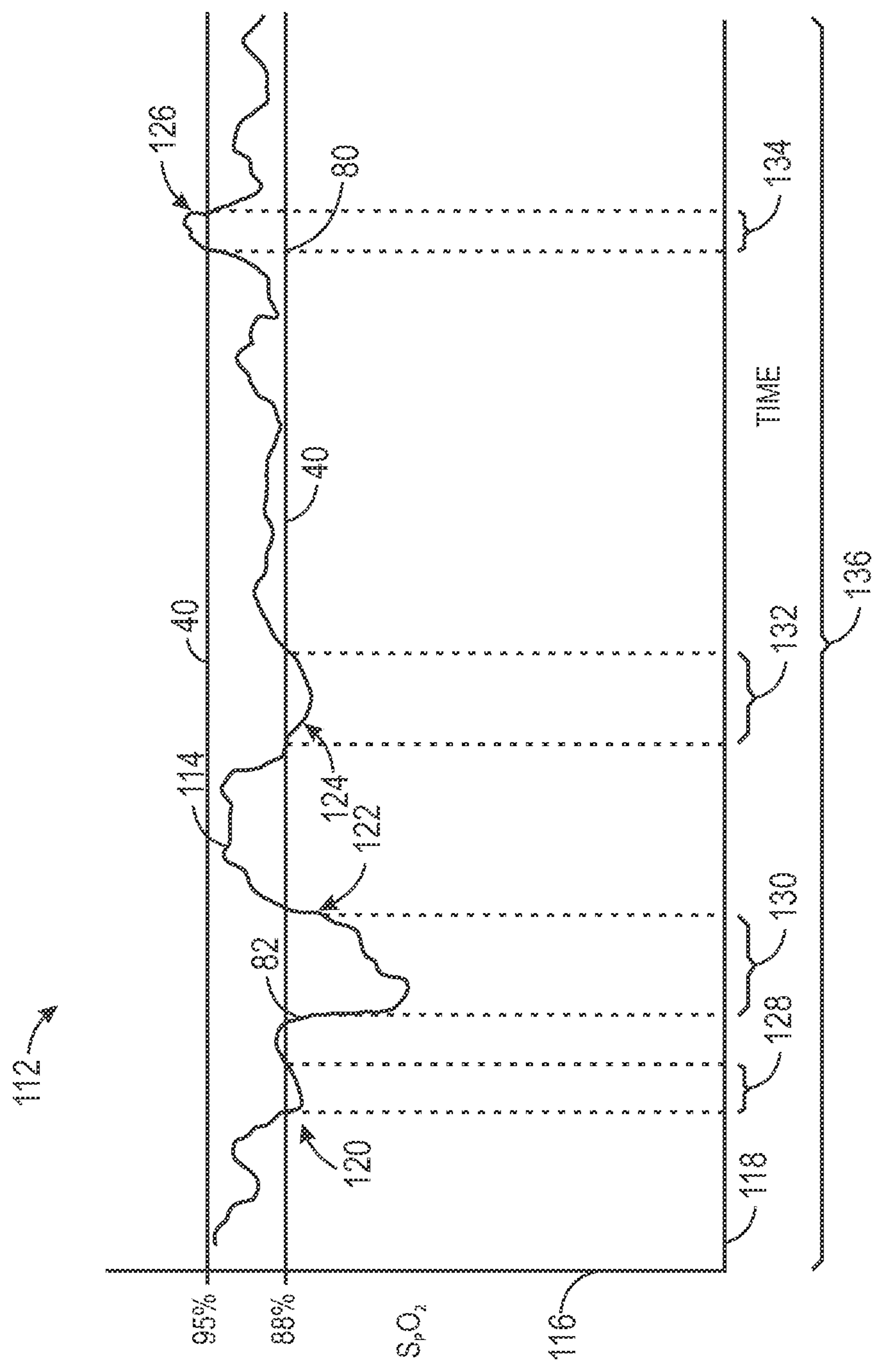
FIG. 4 is a graph depicting a representative plot of a patient's oxygen saturation over time.

FIG. 4 is a graph 112 depicting a representative waveform 114 showing a patient's $SpO_2$ readings, plotted on the y-axis 116, over time, plotted on the x-axis 118. According to certain embodiments, the representative waveform 114 may be employed to calculate the value 42 that is displayed as part of the goal indicator 36A to indicate the percentage of time that oxygen saturation was within the goal limits 40 over a goal time frame 136. According to certain embodiments, the goal time frame 136 may be a rolling period, such as a 24-hour or 12-hour rolling period, among others. However, in other embodiments, the goal time frame 136 may be a set period, such as a 12-hour or 24-hour period starting at a specific time of day. Further, in certain embodiments, the length of the goal time frame 136 may be adjusted by a user through a user interface of the patient monitor 10.

The waveform 114 includes three desaturation events 120, 122, and 124 where the oxygen saturation was below the lower goal limit 40. Further, the waveform 114 includes one oversaturation event 126 where the oxygen saturation was above the upper goal limit 40. Each of the events 120, 122, 124, and 126 has a corresponding time period 128, 130, 132, and 134 that indicates the length of the respective event 120, 122, 124, or 126. Accordingly, the total time that the oxygen saturation was outside of the goal limits 40 may be calculated by summing the time periods 128, 130, 132, and 134. The total time of the events 120, 122, 124, and 126 can then be subtracted from the goal time frame 136 to determine the total time that the oxygen saturation was within the goal limits 40. Finally, the total time that the oxygen saturation was within the goal limits 40 can be divided by the goal time frame 136 to determine the value 42, which indicates the percentage of time that the oxygen saturation was within the goal limits 40.

Figure 5:
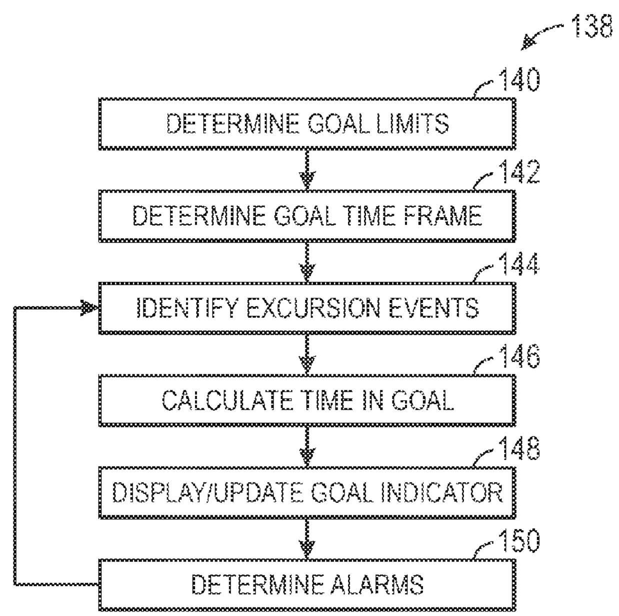
FIG. 5 is a flowchart depicting an embodiment of a method for determining parameters for goal indicators.

FIG. 5 depicts an embodiment of a method 138 for determining parameters for the goal indicator. The method 128 may begin by determining (block 140) the goal limits. For example, the processor 88 may retrieve the goal limits from the ROM 92 or from the nonvolatile storage 96. Further, in certain embodiments, the goal limits may be retrieved from the memory 84 included in the sensor 22. As noted above with respect to FIG. 1, the goal limits may be input through a user interface of the patient monitor 10 for storage within the ROM 92, the nonvolatile storage 96, and/or the memory 84. Further, in certain embodiments, default goal limits may be programmed into the ROM 92, the nonvolatile storage 96, and/or the memory 84 by the manufacturer. The processor 88 also may determine (block 142) the goal time frame. For example, the processor 88 may retrieve the goal time frame from the ROM 92, the nonvolatile storage 96, and/or the memory 84. The goal time frame also may be input through a user interface of the patient monitor 10 for storage within the ROM 92, the nonvolatile storage 96, and/or the memory 84. Further, in certain embodiments, a default goal time frame may be programmed into the ROM 92, the nonvolatile storage 96, and/or the memory 84 by the manufacturer.

The processor 88 may then identify (block 144) excursion events where the physiological parameter is outside of the goal limits. In general, the processor 88 may execute encoded instructions to evaluate the physiological data obtained within the goal time frame to identify events where the data is above and/or below the goal limits. For example, as shown in FIG. 4, the processor 88 may employ one or more algorithms and/or lookup tables stored in the ROM 92 or the nonvolatile storage 96 to compare the $SpO_2$ data to the goal limits 40 and identify the events 120, 122, 124, and 126. The processor 88 also may determine the length of each excursion event and may determine whether each excursion event is above or below the goal limits.

After identifying (block 144) the excursion events, the processor 88 may calculate (block 146) the percentage of time that the physiological parameter was within the goal limits. For example, the processor 88 may subtract the total duration of the excursion events from the goal time frame to determine the total amount of time that the physiological parameter was within the goal limits. The processor 88 may then divide the total amount of time within goal by the goal time frame to determine the percentage of time that the parameter was within the goal limits. According to certain embodiments, the processor 80 may execute encoded instructions stored within the ROM 92 or the nonvolatile storage 96 to calculate the percentage of time that the physiological parameter was within the goal limits.

The patient monitor 10 may then display (block 148) the percentage on the display 18. For example, as shown in FIG. 1, the value 42 may be shown within the goal indicator 36A to indicate the percentage of time that the physiological parameter was within the goal limits. The patient monitor 10 also may update other aspects of the goal indicator 36A. For example, the processor 88 may determine whether the majority of excursion events were above the goal limits or below the goal limits. For example, the processor 88 may employ one or more algorithms or lookup tables to determine whether the number of excursion events that are above the goal limits is greater than the number of excursion events that are below the goal limits. In another example, the processor 88 may determine whether the total time of the excursion events that are above the goal limits is greater than the total time of the excursion events that are below the goal limits. If the majority of excursion events were above the goal limits, the patient monitor may display one type of indicator, such as an up arrow. On the other hand, if the majority of excursion events were below the goal limits, the patient monitor may display another type of indicator, such as a down arrow. In another example, the patient monitor 10 may change the color of the value 42 based on whether the majority of excursion events were above the goal limits or below the goal limits.

The processor 88 also may determine (block 150) whether any alarms should be produced based on the percentage indicated by the value 42. For example, as shown in FIG. 1, the processor 88 may compare the value 42 to the goal threshold 43, which may be stored in the ROM 92, the nonvolatile storage 96, and/or within the memory 84. If the value 42 is below the goal threshold 43, the processor 88 may instruct the monitor 10 to produce an alarm. For example, the monitor 10 may flash the value 42 or may change the color of the value 42. In another example, the monitor 10 may change the color of a graphic, such as goal posts, included within the goal indicator. In yet another example, the monitor 10 may emit an audible alarm through the speaker 60. Further, in yet other embodiments, the monitor 10 may transmit an alarm message to the pager 68 and/or to the central station 64.

After determining (block 150) whether alarms should be produced, the processor 88 may again identify (block 144) excursion events. For example, the processor 88 may evaluate the physiological data that has been received since the last update to the goal indicator to determine whether there are new excursion events. The method 138 may be repeated continuously or at set intervals to update the display of the goal indicator as new physiological data is received.

Figure 6:
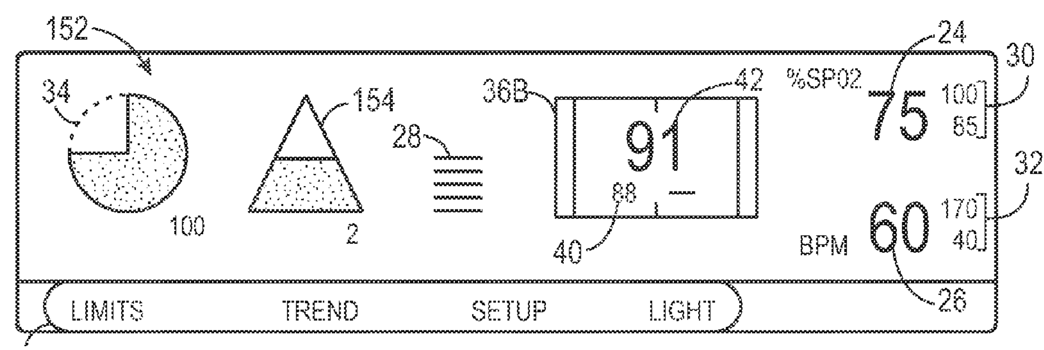
FIG. 6 is a representation of a screen displaying an embodiment of a goal indicator based on oxygen saturation levels.
Figure 7:
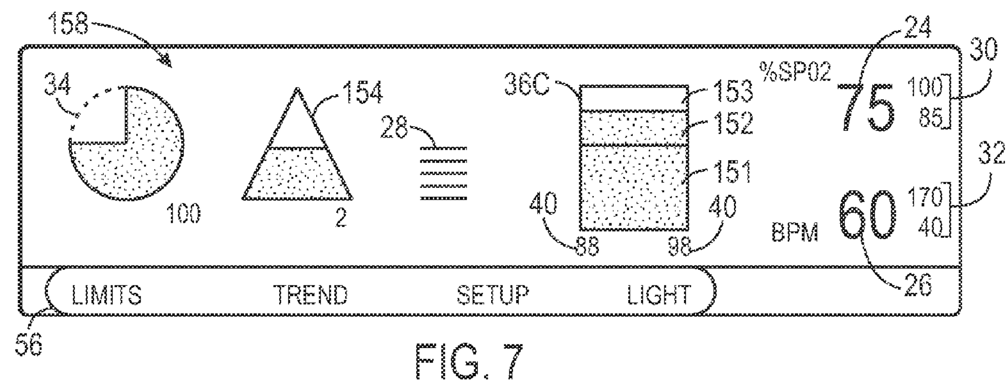
FIG. 7 is a representation of a screen displaying another embodiment of a goal indicator based on oxygen saturation levels.

FIGS. 6 and 7 depict alternate embodiments of goal indicators 36B and 36C that may be shown on the display 18. As shown in FIG. 6, the goal indicator 36B includes the value 42, which is shown within a football field graphic. The goal limits 40 are displayed along the bottom of the graphic. In this embodiment, the lower goal limit is displayed along with a dash indicating that there is no upper goal limit. However, in other embodiments, both upper and lower goal limits may be displayed below the bar graph. Further, in other embodiments, the graphics and/or the relative positions of the values 42 and goal limits 40 may vary. For example, in certain embodiments, the graphic may include the goal posts shown in FIG. 1, or another graphic such as, a bar graph, pie chart, or scoreboard, among others. Further, in certain embodiments, the goal indicators 36B and 36C may include excursion indicators 45 and/or may display the goal threshold 43.

FIG. 7 depicts an embodiment of a goal indicator 36C that includes a bar graph with three regions 151, 152, and 153, that may be used to indicate the percentage of time that the physiological parameter, shown here as oxygen saturation, is within the goal limits 40. In particular, each region 151, 152, and 153 may correspond to a different range of percentages. For example, the region 151 may be filled when the oxygen saturation has been within the goal limits 40 for 0 to 50% of the time; region 152 may be filled when the oxygen saturation has been within the goal limits 40 for 51 to 79% of the time; and region 153 may be filled when the oxygen saturation has been within the goal limits 40 for 80 to 100% of the time. However, in other embodiments, the percentages corresponding to the regions 151, 152, and 153 may vary and/or a different number of regions may be included within the indicator 36C. Further, when one of the upper regions 152 or 153 is filled, the lower regions 152 and/or 151 also may filled. For example, as shown in FIG. 7, the regions 151 and 152 are filled, indicating that the oxygen saturation has been within the goal limits 40 between 50 and 79% of the time.

According to certain embodiments, the region fill color and/or pattern also may change depending on which regions 151, 152, and/or 153 are filled. For example, when the oxygen saturation has been within the goal limits 40 for only 0 to 50% of the time, the region 151 may be filled with a red color. When the oxygen saturation has been within the goal limits 40 for 51 to 79% of the time, the regions 151 and 152 may be filled with a yellow color. Further, when the oxygen saturation has been within the goal limits 40 for 80 to 100% of the time, the regions 151, 152, and 153 may be filled with a green color. Accordingly, the indicator 36C may use both fill level and color to indicate the percentage of time that the physiological parameter has been within the goal limits 40. As shown in FIG. 7, the value 42, which indicates the percentage of time that the physiological parameter is within the goal limits 40, is not shown on the indicator 36C. However, in other embodiments, the value 42 may displayed adjacent to or within the bar graph. Further, as shown in FIG. 7, the goal limits 40 are displayed below the bar graph. However, in other embodiments, the goal limits 40 may not be shown on the indicator 36C. Moreover, in other embodiments, the bar graph may be replaced by another type of graphic, such as a pie chart, among others.

As shown in FIGS. 6 and 7, the goal indicators also may be displayed in conjunction with other types of indicators, such as the SatSeconds™ indicator 34 and the blip bar 28. Further, in certain embodiments, the goal indicators may be displayed in conjunction with a Saturation Pattern Detection ("SPD") indicator 154 that facilitates alarm management. In these embodiments, the patient monitor 10 also may employ an OxiMax SPD™ alert by Nellcor™ to detect patterns of desaturation that are indicative of repetitive reductions in airflow. For example, the OxiMax SPD™ alarm management feature may analyze oxygen saturation trend data to determine if ventilatory instability is present. The Saturation Pattern Detection ("SPD") indicator 154 may provide information to a user related to the occurrence, frequency, and/or magnitude of the patterns detected. As patterns are detected, an index value may increase until the alarm threshold is reached, resulting in an alarm. For example, the index value may be a scoring index, such as a Saturation Pattern Detection index (SPDi), which may represent the magnitude and variability of ventilator variations detected by patterns in the oxygen saturation values. In certain embodiments, the SPDi may be calculated using features such as the magnitude of the $SpO_2$ pattern, the variability in the $SpO_2$ peaks, and the variability in the nadir. In these embodiments, the SPD indicator 154 may gradually fill as the SPDi index increases. When the SPD indicator 154 is full, the tolerance setting may have been reached or exceeded, and the patient monitor 10 may produce an alarm. Moreover, in certain embodiments, an intermediate alarm may be triggered, for example, when the indicator 154 reaches a certain fill level, such as 10%, 25%, or 50%. The SPD alarms may be separate from and independent of the alarms for the goal indicators.

Figure 8:
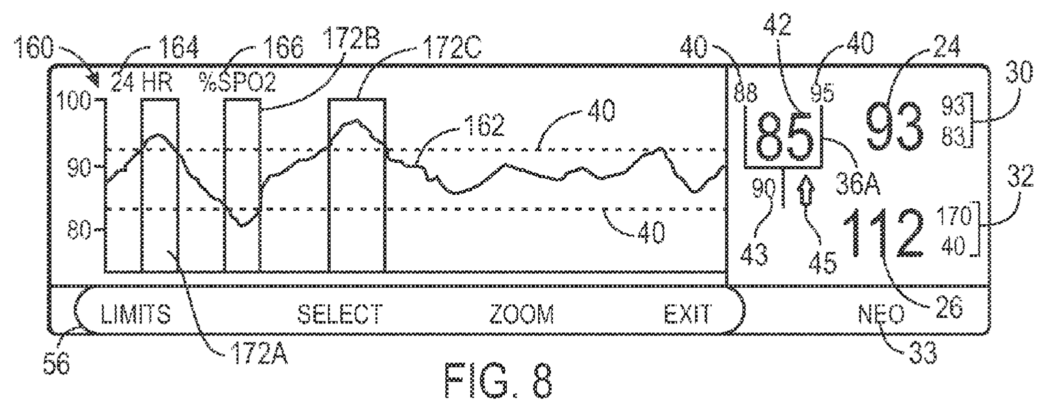
FIG. 8 is a representation of a screen displaying an embodiment of a goal indicator along with trend data.

FIG. 8 depicts a representative screen 160 of the patient monitor 10 that may include the goal indicator 36A. Similar to the screen shown in FIG. 1, the screen 160 includes the oxygen saturation 24, the pulse rate 26, and the alarm limits 30 and 32. The screen 160 also includes the goal indicator 36A, which shows the value 42 that indicates the percentage of time that oxygen saturation was within the goal limits 40. As shown in FIG. 8, the value is currently 85%, which is below the goal threshold of 90%, in this embodiment. Accordingly, in certain embodiments, the patient monitor 10 may emit a visual and/or audible alarm. The goal indicator 36A also includes the excursion indicator 45, which is shown here as an up arrow, indicating that the majority of the excursion events have been above the upper goal limit.

The screen 160 further includes a waveform 162 that represents a patient's $SpO_2$ values over time. According to certain embodiments, the waveform 162 may be a real-time trend of the patient's $SpO_2$ values. A label 164 may be displayed near the waveform 162 to identify the time frame for the trend, shown here as a rolling 24-hour period. According to certain embodiments, the time frame shown by the label 164 also may correspond to the goal time frame used by the patient monitor 10 to calculate the value 42 for the goal indicator 36A. In these embodiments, the waveform 162 may provide a real-time trend view of the data used by the patient monitor 10 to calculate the value 42. Another label 166 also may be displayed near the waveform 162 to identify the physiological parameter that is shown by the trend.

Sections 172 are demarcated on the waveform 162 to indicate excursion events. As shown by the sections 172, the majority of the excursion events have been above the upper goal limit 40, and accordingly the excursion indicator 45 shows an up arrow. Further, in certain embodiments, the sections 172 may have different colors or fill patterns depending on whether the sections 172 identify excursions that are above or below the goal limits. For example, in certain embodiments, the sections 172*a* and 172*c*, which identify excursions that are above the upper goal limit, may be one color while the section 172*b*, which identifies an excursion that is below the lower goal limit, may be another color.

Figure 9:
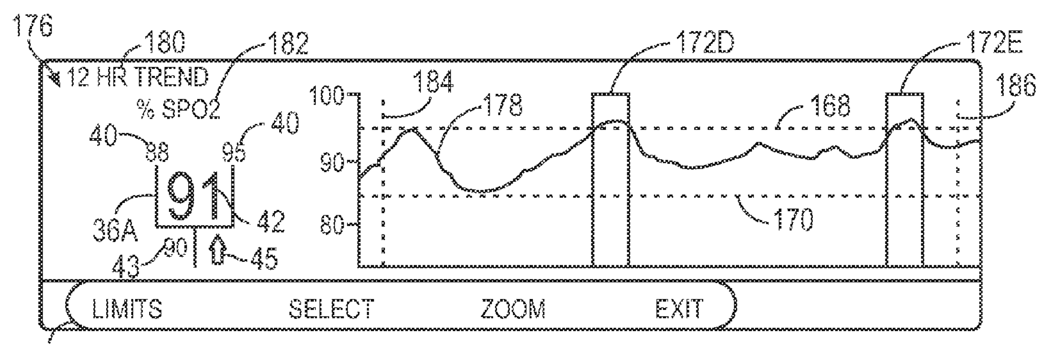
FIG. 9 is a representation of another embodiment of a screen displaying a goal indicator along with trend data.

While FIG. 8 depicts a screen 160 depicting a real-time trend representing a patient's $SpO_2$ values for the most recent time period, FIG. 9 depicts a screen 176 that shows a historical trend that represents a patient's $SpO_2$ values for a previous time period. For example, the screen 176 may be used to show a trend of the patient's $SpO_2$ values for the previous day. As shown in FIG. 9, the goal indicators may be employed to display the percentage of time that a physiological parameter was within predetermined goal limits for a selected previous period of time. The screen 176 includes a waveform 178 that represents a historical trend of a patient's $SpO_2$ values over time. According to certain embodiments, the trend may be accessed by selecting the "TREND" soft key 54B from the screen shown in FIG. 1. A label 164 may be displayed near the waveform 162 to identify the time frame for the trend, which also may correspond to the goal time frame used to calculate the value 42. Another label 182 also may be displayed near the waveform 178 to identify the physiological parameter that is shown by the trend.

The screen 176 includes the goal indicator 36A, which shows the value 42 that indicates the percentage of time that the oxygen saturation was within the goal limits 40 over the trend period. The value 42 may be calculated as described above with respect to blocks 140-148 of FIG. 5, with the trend period being used as the goal time frame. Further, in certain embodiments, the screen 176 also includes cursors 184 and 186 that may be adjusted to change the time frame of the trend. For example, in certain embodiments, the soft keys 54 and the arrow keys 48 shown in FIG. 1, may be employed to move the cursors 184 and 186 to the right and left. After movement of the cursors 184 and 186, the processor 88 may determine the time frame corresponding to the updated trend, for example, using one or more algorithms or lookup tables stored within the ROM 92 or the nonvolatile storage 60. The label 180 may be updated to display the new time frame, and the new time frame also may be employed by the processor 88 to calculate the value 42 shown in the graphical indicator 36A. Accordingly, as the cursors 184 and 186 are moved, the method 138 (FIG. 5) may be performed to display an updated value 42 that shows the percentage of time that the physiological parameters were within the goal limits for the time frame corresponding to the trend.

Figure 10:
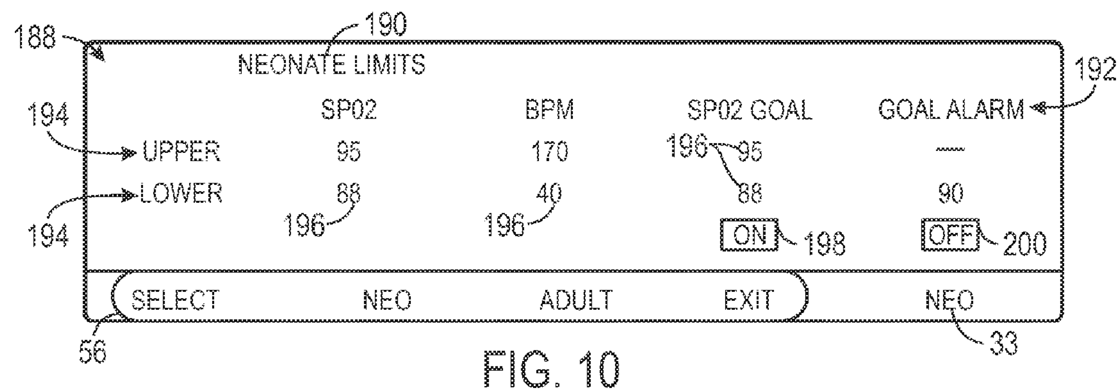
FIG. 10 is a representation of a screen for setting goal parameters and alarms related to goal indicators.

FIG. 10 depicts a screen 188 of the patient monitor that may be employed to adjust parameters of the goal indicator. According to certain embodiments, a user may navigate to the screen 188 by selecting the "LIMITS" soft key 54A from the screen shown in FIG. 1. The screen 188 includes a label 190 that identifies the type of limits (e.g., neonatal or adult) shown on the screen 188. The screen 188 also includes column headers 192 that specify the parameter (e.g., SpO2 alarm limits, pulse rate alarm limits, goal limits, and goal alarm levels) and row headers 194 that specify the type of limit (e.g., upper limit or lower limit). The current settings 196 are shown on the screen 188 in the corresponding row and column headings 194 and 192. For example, as shown on the screen 188, the current goal limits are 88% and 95%, while the goal threshold is set to 90%. The screen 188 also includes settings 198 and 200 for enabling and disabling the use of goal indicators and the goal indicator alarm, respectively. For example, a user may toggle the setting 198 between the on and off position to enable and disable the use and display of goal indicators. In another example, a user may toggle the setting 200 between the on and off position to enable and disable one or more alarms based on the value 42 that shows the percentage of time that the physiological parameters were within the goal limits.

The settings 196, 198, and 200 may be adjusted through the user interface of the patient monitor 10, for example, using the soft keys 54 and the arrow keys 48. Further, in other embodiments, the screen 188 may be shown on the central station 64, and input devices for the central station, such as the touch screen 70, may be employed to adjust the settings 196. The processor 88 may then store the adjusted settings 196, 198, and 200 within the ROM 92, the nonvolatile storage 96, and/or the memory 84 for use during operation of the monitor 10.

Figure 11:
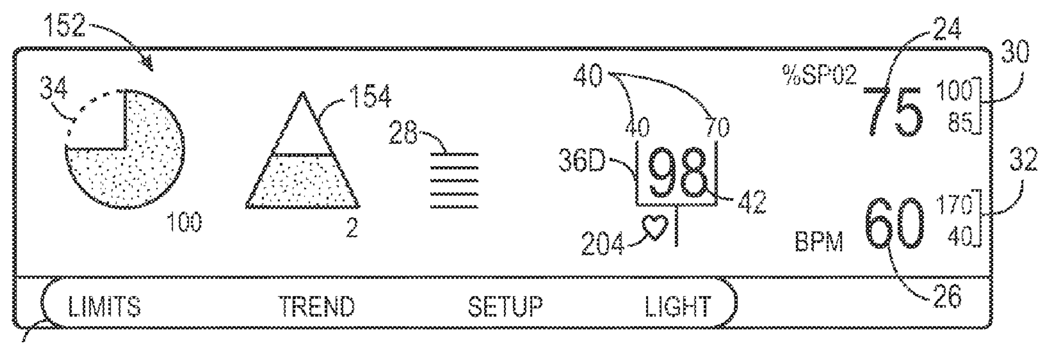
FIG. 11 is a representation of a screen displaying an embodiment of a goal indicator based on pulse rate.

FIG. 11 depicts another embodiment of a goal indicator 36D that may be shown on the display 18. The goal indicator 36D is generally similar to the goal indicators 36A, 36B, and 36C described above with respect to FIGS. 1 to 10, and includes the value 42, and the goal limits 40. However, rather than being based on the physiological parameter of oxygen saturation, the goal indicator 36D is based on the physiological parameter of pulse rate. The goal indicator 36D includes an indicator 204, shown here as a heart graphic, that identifies pulse rate as the physiological parameter. However, in other embodiments, other types of indicators, labels, and/or graphics may be included in the goal indicator to identify the corresponding physiological parameter. Further, in certain embodiments, the goal indicator 36D may include an excursion indicator 45 and/or may display the goal threshold 43.

As may be appreciated, the goal indicators described herein with respect to FIGS. 1 to 11 may be employed for any suitable type of physiological parameter, such as oxygen saturation, pulse rate, blood pressure, temperature, or vital capacity, among others. Further, any combination of the indicators, trends, labels, alarms, and the like may be employed. Moreover, the relative sizes, shapes, geometries, layouts, and locations of the goal indicators may vary. For example, in certain embodiments, the graphical indicators may include other types of graphics such as pie charts or scoreboards, among others.

What is claimed is:

1. A patient monitor, comprising:

a medical device interface suitable for operable connection to a sensor;

a display configured to display patient physiological data based on input received from the sensor and configured to display a goal indicator comprising a numerical value that indicates a percentage of time that the physiological data was within predetermined goal limits during a goal time frame, wherein the goal indicator comprises a graphical representation of goal posts, and wherein the numerical value is displayed between the goal posts; and a processor configured to analyze the patient physiological data to determine the percentage of time that the patient physiological data was within the predetermined goal limits over the goal time frame, to compare the percentage of time to a goal threshold for a minimum percentage of time that the physiological data was within the predetermined goal limits during the goal time frame, to trigger a goal alarm based on the comparison if the percentage of time is below the goal threshold, and to cause the display to display the patient physiological data and the goal indicator.

2. The patient monitor of claim 1, wherein the patient physiological data comprises $SpO_2$ data or pulse rate data.

3. The patient monitor of claim 1, wherein the goal indicator comprises a graphical symbol representing which physiological parameter is analyzed over the goal time frame.

4. The patient monitor of claim 3, wherein the physiological parameter comprises a pulse rate, and wherein the graphical symbol comprises a heart symbol.

5. The patient monitor of claim 1, wherein the goal indicator comprises a fill level representing the percentage of time that the physiological data was within the predetermined goal limits.

6. The patient monitor of claim 1, wherein the goal time frame comprises a rolling period, and wherein the processor is configured to identify the patient physiological data that corresponds to the rolling period.

7. The patient monitor of claim 1, wherein the processor is configured to analyze the patient physiological data to identify excursion events where the patient physiological data is outside of the predetermined goal limits and to determine the percentage of time that the physiological data was within predetermined goal limits during the goal time frame based at least in part upon a summation of a duration for each identified excursion event.

8. The patient monitor of claim 7, wherein the processor is configured to determine whether the majority of the excursion events are above or below the predetermined goal limits, and wherein the goal indicator comprises a non-numerical graphical indicator that indicates whether the majority of the excursion events during the goal time frame were above or below the predetermined goal limits.

9. A pulse oximeter, comprising:

a medical device interface suitable for operable connection to a sensor;

a display configured to display oxygen saturation levels based on input received from the sensor and configured to display a goal indicator comprising a value that indicates the percentage of time that the oxygen saturation levels were within predetermined goal limits during a goal time frame; and a processor configured to analyze the oxygen saturation levels to determine the value, to compare the value to a goal threshold, to trigger a goal alarm in response to detecting that the value is below the goal threshold, and to cause the display to display the oxygen saturation levels and the goal indicator.

10. The pulse oximeter of claim 9, wherein the predetermined goal limits comprise an upper limit, or a lower limit, or a combination thereof.

11. The pulse oximeter of claim 9, wherein the processor is configured to trigger an oxygen saturation alarm in response to determining that one or more of the oxygen saturation levels is outside of an oxygen saturation limit, and wherein the goal alarm is triggered independently from the oxygen saturation alarm.

12. The pulse oximeter of claim 9, wherein the goal indicator comprises the predetermined goal limits and the goal threshold both displayed adjacent to the value.

13. The pulse oximeter of claim 9, wherein the processor is configured to update the value in response to receiving new input from the sensor.

14. The pulse oximeter of claim 9, wherein the pulse oximeter comprises a graphical user interface configured to receive a user input that alters the goal time frame, or the predetermined goal limits, or a combination thereof.

15. A method, comprising:

determining, via a patient monitor, oxygen saturation levels based on data received from a physiological sensor;

comparing, via the patient monitor, the oxygen saturation levels to one or more alarm limits;

providing, via the patient monitor, an alarm indication based at least in part on the oxygen saturation levels being outside of the one or more alarm limits;

comparing, via the patient monitor, the oxygen saturation levels to one or more goal limits to identify excursion events where the oxygen saturation levels are outside of the one or more goal limits;

calculating, via the patient monitor, based on the excursion events and a goal time frame, a percentage of time that the oxygen saturation levels were within the goal limits;

providing, via the patient monitor, a goal alarm indication based at least in part on a determination that the percentage of time that the oxygen saturation levels were within the goal limits over the goal time frame is less than a goal threshold; and displaying the percentage on a patient monitor.

16. The method of claim 15, wherein comparing the oxygen saturation levels to one or more goal limits comprises determining whether the oxygen saturation levels are greater than an upper goal limit and determining whether the oxygen saturation levels are less than a lower goal limit.

17. The method of claim 15, wherein calculating a percentage of time comprises determining a total duration of the excursion events.

18. The method of claim 15, comprising setting, via the patient monitor, the goal time frame to a trend time frame of a historical trend displayed on the patient monitor.

19. The method of claim 15, comprising storing, via the patient monitor, the one or more goal limits or the value, or a combination thereof, on a memory of the physiological sensor.

20. The method of claim 15, wherein a lower goal limit of the one or more goal limits is greater than a lower alarm limit of the one or more alarm limits.

* * * * *